US011801014B2

(12) United States Patent
Kimura

(10) Patent No.: US 11,801,014 B2
(45) Date of Patent: Oct. 31, 2023

(54) BIOPOTENTIAL MEASUREMENT DEVICE AND NON-TRANSITORY COMPUTER READABLE MEDIUM

(71) Applicant: FUJIFILM BUSINESS INNOVATION CORP., Tokyo (JP)

(72) Inventor: Tsutomu Kimura, Kanagawa (JP)

(73) Assignee: FUJIFILM Business Innovation Corp., Tokyo (JP)

(*) Notice: Subject to any disclaimer, the term of this patent is extended or adjusted under 35 U.S.C. 154(b) by 401 days.

(21) Appl. No.: 16/897,829

(22) Filed: Jun. 10, 2020

(65) Prior Publication Data

US 2021/0196205 A1 Jul. 1, 2021

(30) Foreign Application Priority Data

Dec. 25, 2019 (JP) .................... 2019-234480

(51) Int. Cl.
*H03M 1/12* (2006.01)
*A61B 5/00* (2006.01)
*A61B 5/375* (2021.01)

(52) U.S. Cl.
CPC ............ *A61B 5/7225* (2013.01); *A61B 5/375* (2021.01); *A61B 5/6803* (2013.01); *H03M 1/12* (2013.01)

(58) Field of Classification Search
CPC ...................................................... H03M 1/12
See application file for complete search history.

(56) References Cited

U.S. PATENT DOCUMENTS

| | | | |
|---|---|---|---|
| 10,615,818 B1* | 4/2020 | Singh ................... | H03M 3/496 |
| 10,693,483 B1* | 6/2020 | Luo ...................... | H03M 1/0836 |
| 10,812,097 B1* | 10/2020 | Milicevic ............... | H03M 1/36 |
| 2016/0126967 A1* | 5/2016 | Oh ........................ | H03M 1/06 |
| | | | 341/118 |
| 2016/0189583 A1* | 6/2016 | Cho ...................... | G09G 3/20 |
| | | | 345/204 |
| 2016/0248432 A1* | 8/2016 | Naderi Alizadeh ... | H03M 1/002 |
| 2018/0317853 A1 | 11/2018 | Fan et al. | |
| 2019/0115931 A1* | 4/2019 | Hurwitz ................. | H03M 1/56 |
| 2022/0123973 A1* | 4/2022 | Kim .................. | H04L 25/03114 |

FOREIGN PATENT DOCUMENTS

JP 2001-61800 A 3/2001

\* cited by examiner

*Primary Examiner* — Lam T Mai
(74) *Attorney, Agent, or Firm* — Oliff PLC

(57) ABSTRACT

A biopotential measurement device includes: a branching section that branches a biopotential into plural analog potentials; a first conversion section that converts one of the analog potentials branched by the branching section into a digital potential on the basis of a designated first conversion condition; and a second conversion section that converts the other of the analog potentials branched by the branching section into a digital potential on the basis of a second conversion condition. The amount of data obtained after a conversion with the second conversion condition is smaller than the amount of data obtained after a conversion with the first conversion condition.

20 Claims, 8 Drawing Sheets

FIG. 5

```
POTENTIAL CONVERSION SECTION 1
    ACQUISITION FREQUENCY SET VALUE    (INPUT VALUE) Hz
    DECOMPOSITION PRECISION            (INPUT VALUE) bit POTENTIAL CONVERSION SECTION 2
    PROCESSING OPERATION               On/Off
    ACQUISITION FREQUENCY SET VALUE    (INPUT VALUE) Hz
    DECOMPOSITION PRECISION            (INPUT VALUE) bit POTENTIAL CONVERSION SECTION 3
    PROCESSING OPERATION               On/Off
    ACQUISITION FREQUENCY SET VALUE    (INPUT VALUE) Hz
    DECOMPOSITION PRECISION            (INPUT VALUE) bit
        ⋮                                      ⋮
```

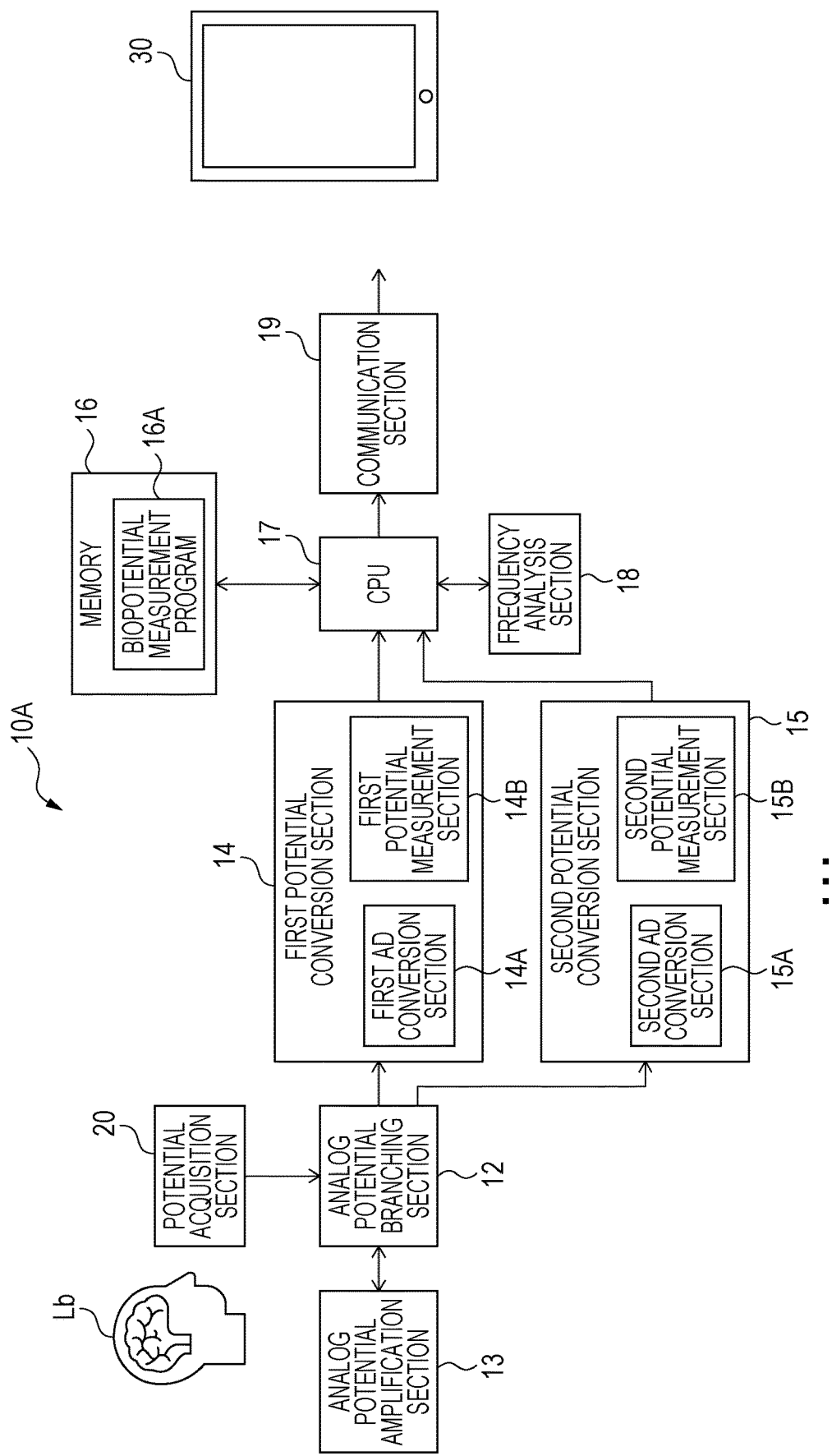

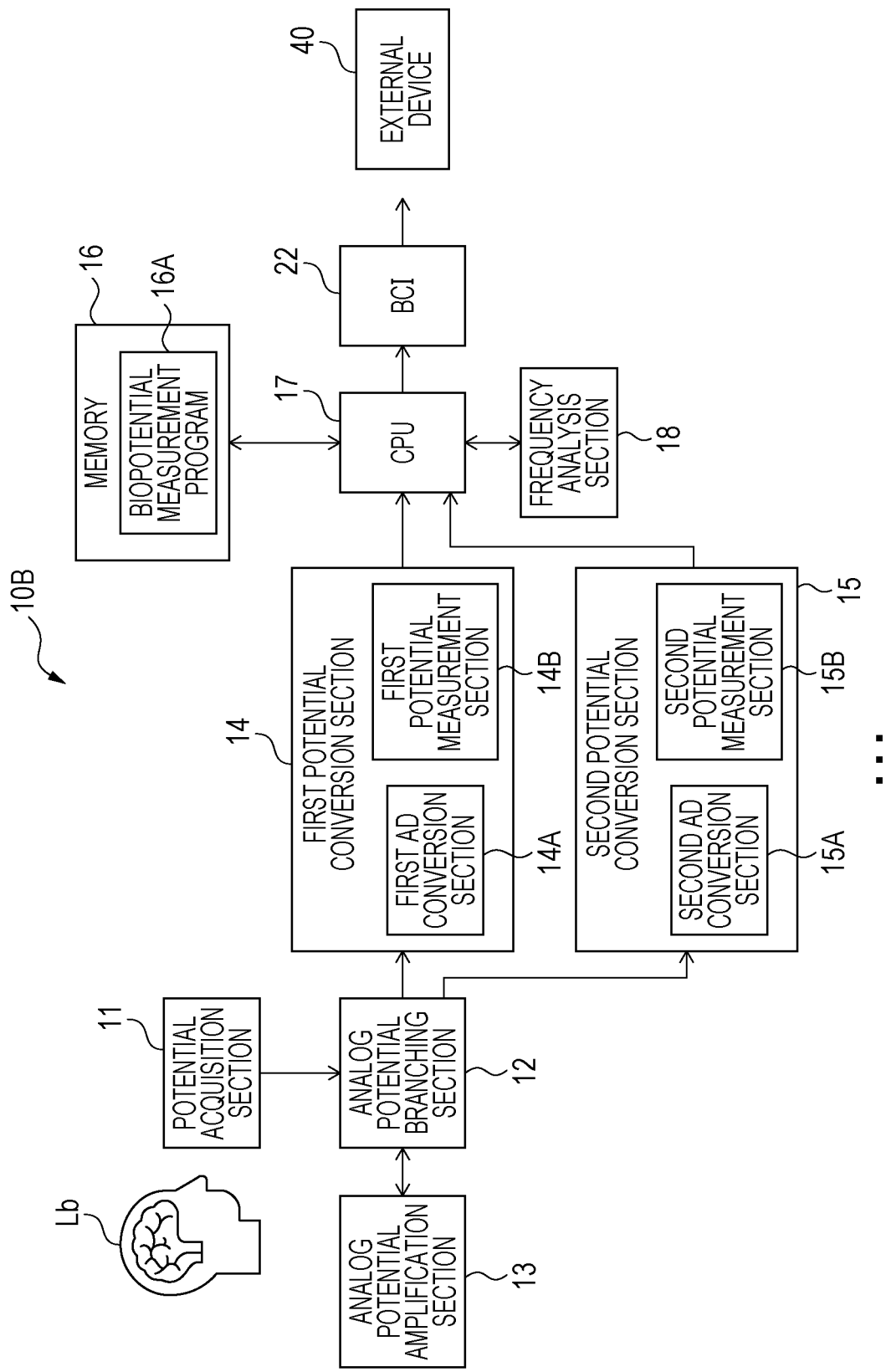

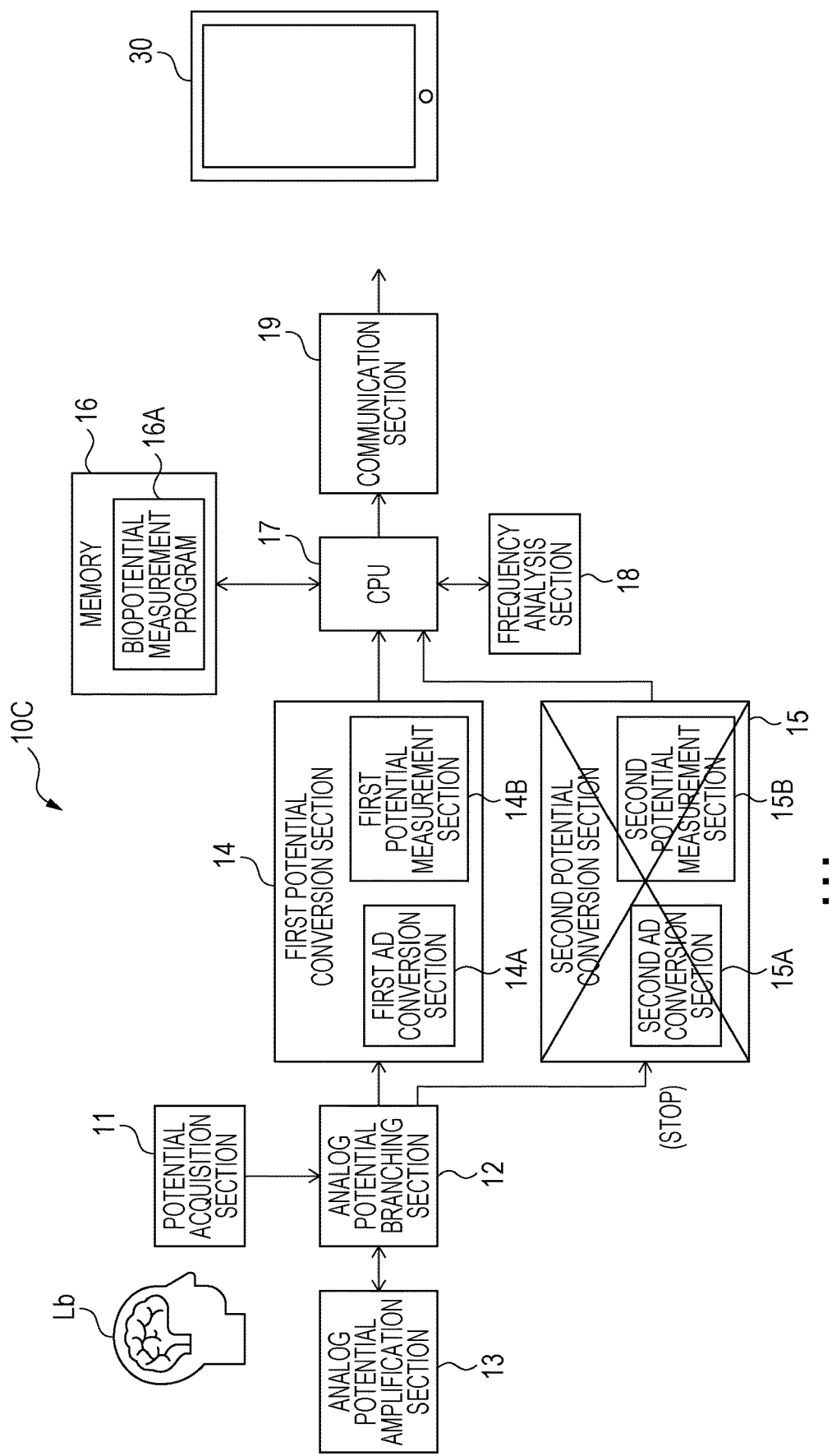

BIOPOTENTIAL MEASUREMENT DEVICE AND NON-TRANSITORY COMPUTER READABLE MEDIUM

CROSS-REFERENCE TO RELATED APPLICATIONS

This application is based on and claims priority under 35 USC 119 from Japanese Patent Application No. 2019-234480 filed Dec. 25, 2019.

BACKGROUND

(i) Technical Field

The present disclosure relates to a biopotential measurement device and a non-transitory computer readable medium.

(ii) Related Art

Japanese Unexamined Patent Application Publication No. 2001-61800, for example, describes a brain wave signal processing device that analyzes time-series data on a brain wave detected by a brain wave detection device to reconfigure a brain wave signal from which a noise component due to a predetermined biological phenomenon has been removed. The brain wave signal processing device includes a decomposition unit that performs a wavelet decomposition of the time-series data on the brain wave to a predetermined decomposition level, and a reconfiguration unit that reconfigures a brain wave signal from which a noise component due to a predetermined biological phenomenon has been removed by combining high-frequency components to the predetermined decomposition level, excluding low-frequency components, included in the result of the decomposition to the predetermined decomposition level obtained by the decomposition unit.

SUMMARY

A brain wave potential generated from a human body is a continuous analog potential, for example. In order to read various events from the brain wave potential, it is necessary to frequency-decompose the analog potential of the brain wave potential and classify the potential in accordance with the magnitude of the amplitude thereof. Therefore, the continuous analog potential is converted into discrete digital potentials. The frequency acquired from the analog potential may be increased in order to approximate the discrete digital potentials to the continuous potential.

However, increasing the frequency increases the amount of data, which may tighten the memory capacity, shorten the data saving time, etc. Therefore, it is desired to reduce the amount of data while measuring a biopotential with a high precision.

Aspects of non-limiting embodiments of the present disclosure relate to providing a biopotential measurement device and a non-transitory computer readable medium that allow obtaining a biopotential with a small amount of data while measuring the biopotential with a high precision compared to a case where an analog biopotential is converted into digital potentials using a single conversion condition.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided a biopotential measurement device including: a branching section that branches a biopotential into a plurality of analog potentials; a first conversion section that converts one of the analog potentials branched by the branching section into a digital potential on a basis of a designated first conversion condition; and a second conversion section that converts the other of the analog potentials branched by the branching section into a digital potential on a basis of a second conversion condition, an amount of data obtained after a conversion with the second conversion condition being smaller than an amount of data obtained after a conversion with the first conversion condition.

BRIEF DESCRIPTION OF THE DRAWINGS

Exemplary embodiments of the present disclosure will be described in detail based on the following figures, wherein:

FIG. 5 is a front view illustrating an example of a reception screen according to the exemplary embodiment;

FIG. 7 is a block diagram illustrating an example of the electrical configuration of a biopotential measurement device according to a second exemplary embodiment;

FIG. 8 is a block diagram illustrating an example of the electrical configuration of a biopotential measurement device according to a third exemplary embodiment; and FIG. 9 is a block diagram illustrating an example of the electrical configuration of a biopotential measurement device according to a fourth exemplary embodiment.

DETAILED DESCRIPTION

Exemplary embodiments of the present disclosure will be described in detail below with reference to the drawings.

First Exemplary Embodiment

Figure 1:
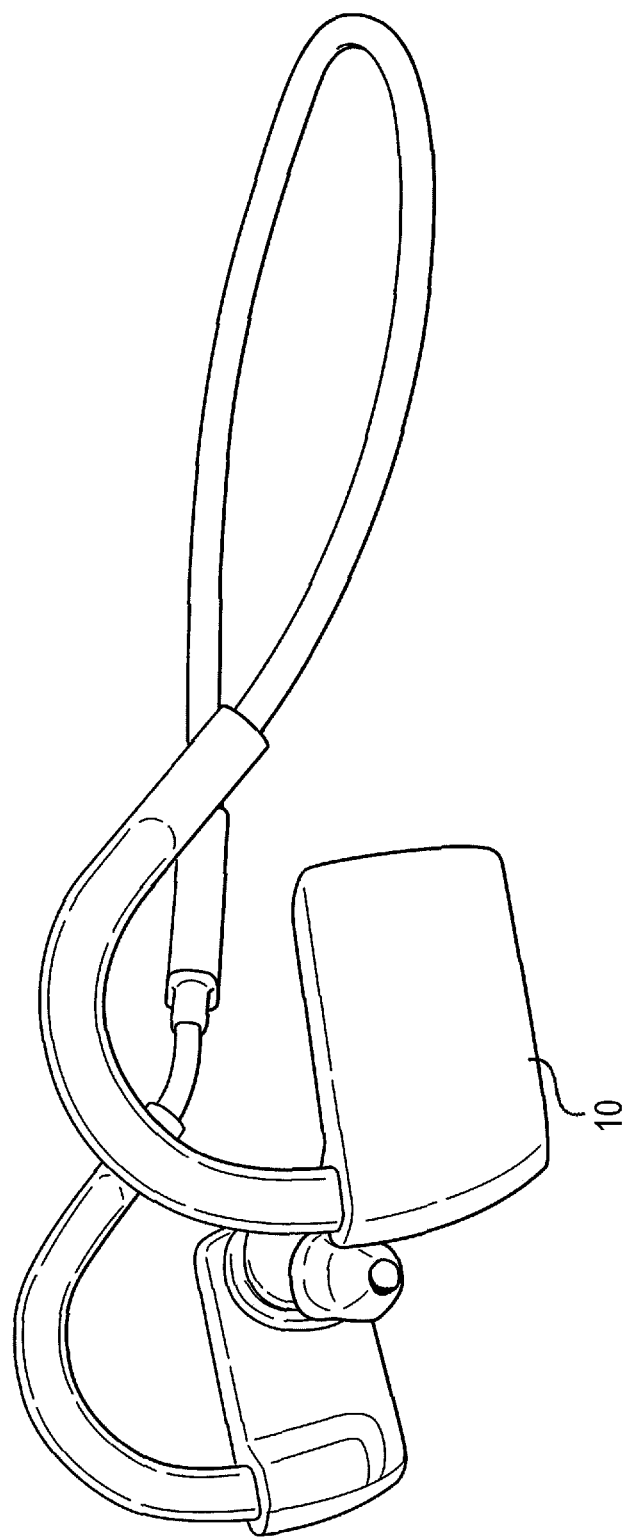
FIG. 1 illustrates an example of the appearance of a biopotential measurement device according to a first exemplary embodiment.

FIG. 1 illustrates an example of the appearance of a biopotential measurement device 10 according to a first exemplary embodiment.

By way of example, a simple electroencephalograph of an earphone type is applied to the biopotential measurement device 10 according to the present exemplary embodiment. The simple electroencephalograph may be an electroencephalograph which uses a single-channel (1-ch) dry electrode, for example. In this case, the biopotential measurement device 1 is mountable on the ears of a person to be measured, and acquires a biopotential from the external auditory meatus of the ears. Examples of the biopotential include a brain wave potential, a pulse wave potential, and a myoelectric potential. Examples of the biological body to be measured include a human. It should be noted, however, that the biological body to be measured may not be a human, and may be a dog, a cat, etc., for example.

Most simple electroencephalographs according to the related art are of a headset type, a headgear type, etc., and are mountable on the head portion. Such a simple electroencephalograph of a headset type or a headgear type is susceptible to motion of the person to be measured, and it may be difficult to keep the electrode in stable contact with the person to be measured. Therefore, the biopotential obtained from the person to be measured is occasionally unstable. Further, the person to be measured may look unnatural when he/she wears the simple electroencephalograph, which makes the simple electroencephalograph unsuitable for daily use. Therefore, the simple electroencephalograph is limited to entertainment use such as use during game play.

On the contrary, the simple electroencephalograph of an earphone type according to the present exemplary embodiment includes earpiece electrodes constituted of conductive rubber to be mountable on the ears of the person to be measured like earphones, and therefore is insusceptible to motion of the person to be measured and secures stable contact with the person to be measured. Further, the person to be measured may look natural when he/she wears the simple electroencephalograph, which makes the simple electroencephalograph suitable for daily use.

Figure 2:
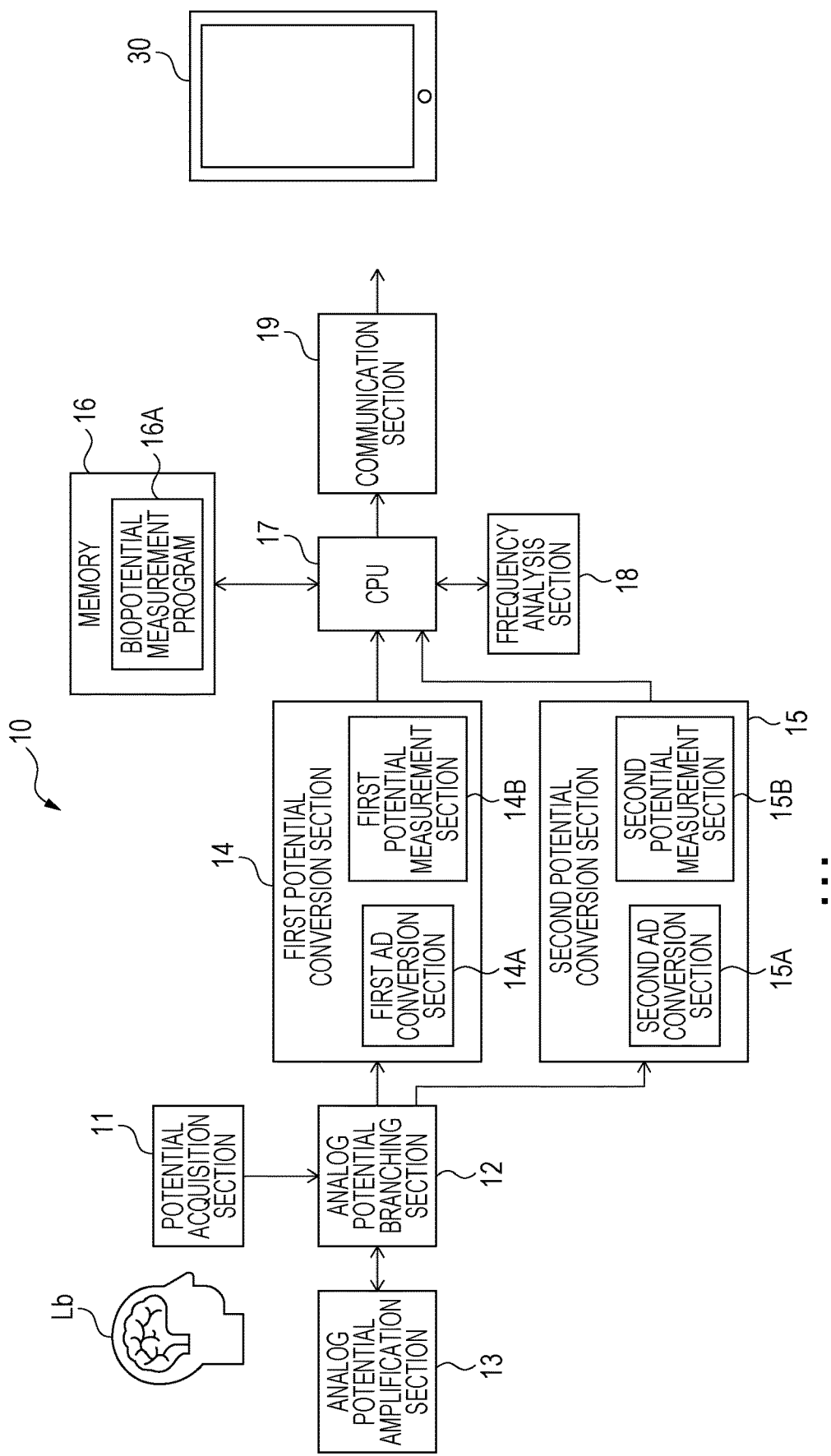
FIG. 2 is a block diagram illustrating an example of the electrical configuration of the biopotential measurement device according to the first exemplary embodiment.

FIG. 2 is a block diagram illustrating an example of the electrical configuration of the biopotential measurement device 10 according to the first exemplary embodiment.

As illustrated in FIG. 2, the biopotential measurement device 10 according to the present exemplary embodiment includes a potential acquisition section 11, an analog potential branching section 12, an analog potential amplification section 13, a first potential conversion section 14, a second potential conversion section 15, a memory 16, a central processing unit (CPU) 17, a frequency analysis section 18, and a communication section 19. The first potential conversion section 14 includes a first analog-digital (AD) conversion section 14A and a first potential measurement section 14B. The second potential conversion section 15 includes a second AD conversion section 15A and a second potential measurement section 15B. While two potential conversion sections are provided in the present exemplary embodiment, three or more potential conversion sections may also be provided.

The analog potential branching section 12, the analog potential amplification section 13, the first potential conversion section 14, and the second potential conversion section 15 described above are each constituted as an electric circuit.

The potential acquisition section 11 acquires a biopotential of a person to be measured Lb. The potential acquisition section 11 includes earpiece electrodes that are mountable to the ears of the person to be measured Lb, for example. The biopotential of the person to be measured Lb is acquired using the earpiece electrodes as contact points. The biopotential to be acquired is an analog potential.

The analog potential branching section 12 branches the biopotential acquired by the potential acquisition section 11 into a plurality of analog potentials, supplies one of the branched analog potentials to the first AD conversion section 14A, and supplies the other of the branched analog potentials to the second AD conversion section 15A. The analog potential branching section 12 is an example of a branching section.

The analog potential amplification section 13 is connected to the analog potential branching section 12, amplifies the biopotential obtained via the analog potential branching section 12, and feeds the amplified biopotential to the analog potential branching section 12.

The first AD conversion section 14A converts one of the analog potentials branched by the analog potential branching section 12 into a digital potential on the basis of a designated first conversion condition. The first AD conversion section 14A is an example of a first conversion section.

The second AD conversion section 15A converts the other of the analog potentials branched by the analog potential branching section 12 into a digital potential on the basis of a designated second conversion condition. The amount of data obtained after a conversion with the second conversion condition is smaller than the amount of data obtained after a conversion with the first conversion condition. The second AD conversion section 15A is an example of a second conversion section.

The first potential measurement section 14B measures a biopotential from the digital potential obtained through the conversion performed by the first AD conversion section 14A, and supplies the measured biopotential to the CPU 17. Specifically, the first potential measurement section 14B filters a noise signal contained in the digital potential. The first potential measurement section 14B is an example of a first measurement section.

The second potential measurement section 15B measures a biopotential from the digital potential obtained through the conversion performed by the second AD conversion section 15A, and supplies the measured biopotential to the CPU 17. Specifically, the second potential measurement section 15B filters a noise signal contained in the digital potential. The second potential measurement section 15B is an example of a second measurement section.

The memory 16 may be a non-volatile storage medium such as a read only memory (ROM), an electrically erasable programmable read-only memory (EEPROM), and a flash memory, for example. The memory 16 stores a biopotential measurement program 16A according to the present exemplary embodiment. The biopotential measurement program 16A is a program for controlling biopotential measurement operation of the biopotential measurement device 10. The biopotential measurement program 16A controls each of the analog potential branching section 12, the analog potential amplification section 13, the first potential conversion section 14, and the second potential conversion section 15 discussed above.

The biopotential measurement program 16A may be installed in advance in the biopotential measurement device 10, for example. The biopotential measurement program 16A may be stored in a non-volatile storage medium, or distributed via a network, to be installed, as appropriate, in the biopotential measurement device 10 to be implemented. Examples of the non-volatile storage medium are assumed to include a Compact Disc Read Only Memory (CD-ROM), a magneto-optical disk, a hard disk drive (HDD), a Digital Versatile Disc Read Only Memory (DVD-ROM), a flash memory, and a memory card.

The CPU 17 is connected so as to be communicable with the various sections that constitute the biopotential measurement device 10, and controls operation of the various sections. The CPU 17 controls operation of the analog potential branching section 12, the analog potential amplification section 13, the first potential conversion section 14, and the second potential conversion section 15 discussed above by reading and executing the biopotential measurement program 16A stores in the memory 16.

The frequency analysis section 18 decomposes the biopotential supplied to the CPU 17 into frequencies, or frequency bands such as alpha waves, beta waves, theta waves, and delta waves, by performing a frequency analysis on the biopotential using a Fourier transform etc., by way of example.

The communication section 19 is a communication interface for near-field wireless communication such as Wi-Fi (registered trademark), Bluetooth (registered trademark), and NFC (near field communication), for example. The communication section 19 enables near-field wireless communication with a terminal device 30 such as a personal computer (PC), a smartphone, and a tablet terminal, for example.

The first conversion condition and the second conversion condition may be a frequency acquired from the analog potential, by way of example. As discussed above, the amount of data obtained after a conversion with the second conversion condition is smaller than the amount of data obtained after a conversion with the first conversion condition. In this case, the frequency for the second conversion condition is lower than the frequency for the first conversion condition. Such conditions will be specifically described with reference to FIG. 3.

Figure 3:
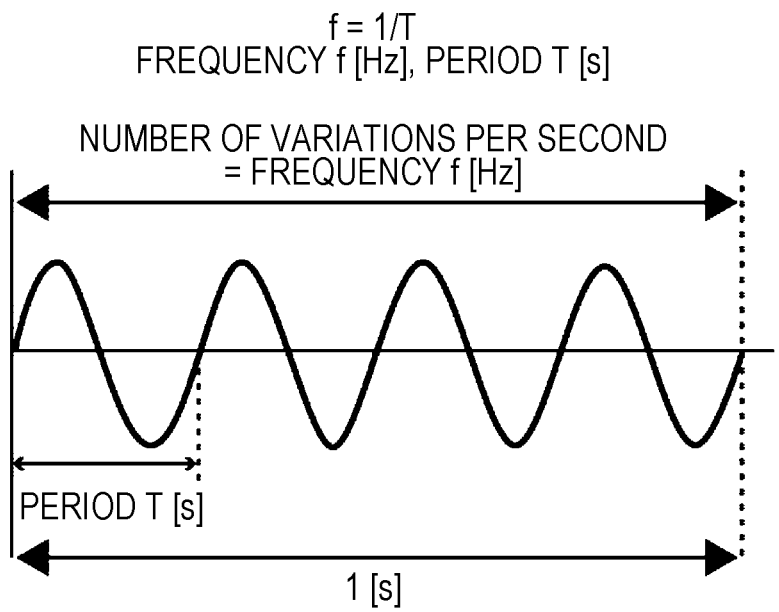
FIG. 3 illustrates the relationship between the frequency and the period according to the exemplary embodiment.

FIG. 3 illustrates the relationship between the frequency and the period according to the present exemplary embodiment.

As illustrated in FIG. 3, a frequency f [Hz] and a period T [s (second)] has a relationship f=1/T. In order to analyze each period of the frequency f to be analyzed with the same number of data, that is, analyze each period with the same analysis precision, it is necessary to vary the frequency (hereinafter referred to as an "acquisition frequency") acquired from the analog potential. If the acquisition frequency is ten times, for example, the amount of data is ten times, and the data saving time is one-tenth. If the amount of data for each period is large, the frequency analysis takes a long processing time.

In example 1, in the case where one piece of data is acquired at an acquisition frequency of f=100 [Hz], that is, at a period of T=1/100 [s], ten pieces of data are provided per period for a biopotential (e.g. a brain wave potential) at an acquisition frequency of 10 [Hz], that is, at a period of 1/10 [s]. Two pieces of data are provided per period for a biopotential (e.g. a brain wave potential) at an acquisition frequency of 50 [Hz], that is, at a period of 1/50 [s]. One piece of data is provided per period for a biopotential (e.g. a brain wave potential) at an acquisition frequency of 100 [Hz], that is, at a period of 1/100 [s]. In this case, the amount of data for one second is 8 bits/data×100=0.1 kilobytes.

In example 2, in the case where one piece of data is acquired at an acquisition frequency of f=500 [Hz], that is, at a period of T=1/500 [s], fifty pieces of data are provided per period for a biopotential (e.g. a brain wave potential) at an acquisition frequency of 10 [Hz], that is, at a period of 1/10 [s]. Ten pieces of data are provided per period for a biopotential (e.g. a brain wave potential) at an acquisition frequency of 50 [Hz], that is, at a period of 1/50 [s]. Five pieces of data are provided per period for a biopotential (e.g. a brain wave potential) at an acquisition frequency of 100 [Hz], that is, at a period of 1/100 [s]. In this case, the amount of data for one second is 8 bits/data×500=0.5 kilobytes.

In example 3, in the case where one piece of data is acquired at an acquisition frequency of f=1000 [Hz], that is, at a period of T=1/1000 [s], one hundred pieces of data are provided per period for a biopotential (e.g. a brain wave potential) at an acquisition frequency of 10 [Hz], that is, at a period of 1/10 [s]. Twenty pieces of data are provided per period for a biopotential (e.g. a brain wave potential) at an acquisition frequency of 50 [Hz], that is, at a period of 1/50 [s]. Ten pieces of data are provided per period for a biopotential (e.g. a brain wave potential) at an acquisition frequency of 100 [Hz], that is, at a period of 1/100 [s]. In this case, the amount of data for one second is 8 bits/data×1000=1.0 kilobytes.

It is seen from the above examples that the amount of data after a conversion is reduced by lowering the acquisition frequency.

Alternatively, the first conversion condition and the second conversion condition may be the potential range and the potential resolution of potentials acquired from the analog potential. In this case, the ratio between the potential range and the potential resolution for the second conversion condition is lower than the ratio between the potential range and the potential resolution for the first conversion condition. Such conditions will be specifically described with reference to FIG. 4.

Figure 4:
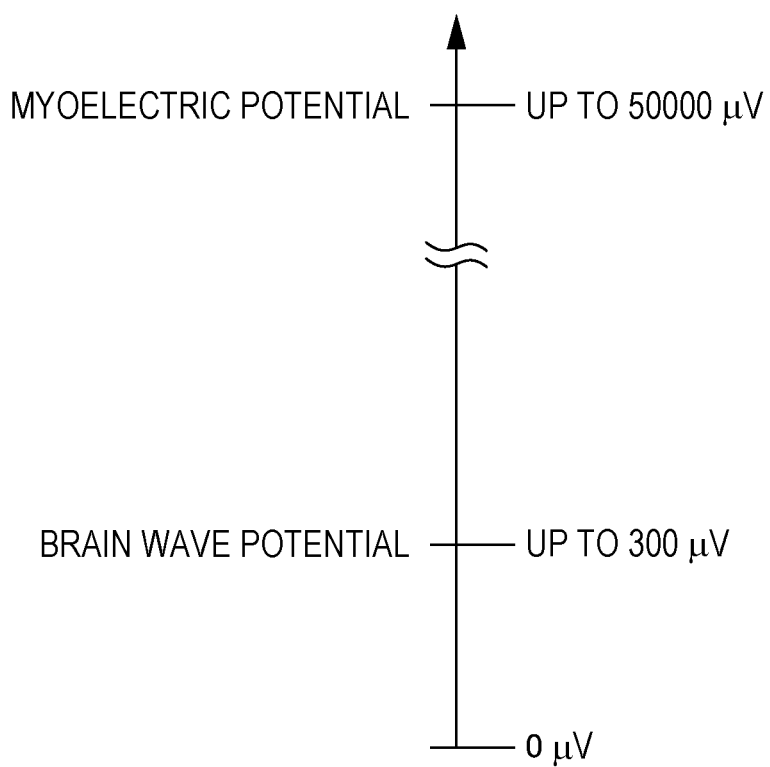
FIG. 4 illustrates the relationship between the type of biopotentials and the potential range according to the exemplary embodiment.

FIG. 4 illustrates the relationship between the type of biopotentials and the potential range according to the present exemplary embodiment.

As illustrated in FIG. 4, the potential range is different in accordance with the type of the biopotential. In the case of a brain wave potential, by way of example, the potential range is 5 [μV] or more and 300 [μV] or less, and the frequency is 0 [Hz] or more and 150 [Hz] or less. In the case of a myoelectric potential, by way of example, the potential range is 100 [μV] or more and 50000 [μV] or less, and the frequency is 0 [Hz] or more and 10000 [Hz] or less. In the case of an ocular potential, by way of example, the potential range is 50 [μV] or more and 3500 [μV] or less, and the frequency is 0 [Hz] or more and 50 [Hz] or less. In the case of a nerve potential, by way of example, the potential range is 10 [μV] or more and 3000 [μV] or less, and the frequency is 0 [Hz] or more and 10000 [Hz] or less. In the case of a pulse wave potential for arteries and veins, by way of example, the potential range is 500 [μV] or more and 4000 [μV] or less, and the frequency is 0 [Hz] or more and 250 [Hz] or less. In the case of a pulse wave potential for capillaries, however, the potential range is lower.

In this case, the amount of data after a conversion may be reduced by varying the ratio between the potential range (hereinafter referred to as a "potential acquisition range") and the potential resolution (hereinafter referred to as a "potential acquisition resolution") of potentials acquired from the analog potential.

In example 1, in the case where the potential acquisition range is 0 [μV] or more and 100 [μV] or less and the potential acquisition resolution is 0.5 [μV], the number of bits (amount of data) per piece of data is 8 bits. This is because the ratio between the potential acquisition range and the potential acquisition resolution is 100/0.5 and thus data are acquired as divided by the eighth power of 2 (=256).

In example 2, in the case where the potential acquisition range is 0 [μV] or more and 10000 [μV] or less and the potential acquisition resolution is 0.5 [μV], the number of bits (amount of data) per piece of data is 15 bits. This is because the ratio between the potential acquisition range and the potential acquisition resolution is 10000/0.5 and thus data are acquired as divided by the fifteenth power of 2 (=32768).

In example 3, in the case where the potential acquisition range is 0 [μV] or more and 10000 [μV] or less and the potential acquisition resolution is 10 [μV], the number of bits (amount of data) per piece of data is 10 bits. This is because the ratio between the potential acquisition range and the potential acquisition resolution is 10000/10 and thus data are acquired as divided by the tenth power of (=1024).

It is seen from the above examples that the amount of data after a conversion is reduced by reducing the ratio between the potential acquisition range and the potential acquisition resolution.

Alternatively, the first conversion condition and the second conversion condition may each be set in advance in accordance with the purpose of use of the biopotential. In this case, the CPU 17 performs control so as to display a reception screen illustrated in FIG. 5 on the terminal device 30, by way of example. The CPU 17 is an example of a controller.

FIG. 5 is a front view illustrating an example of the reception screen according to the exemplary embodiment.

The reception screen illustrated in FIG. 5 is a screen for receiving setting of each of the first conversion condition and the second conversion condition. While three potential conversion sections are provided in the example in FIG. 5, it is only necessary that two or more potential conversion sections should be provided.

As illustrated in FIG. 5, for a potential conversion section 1, a set value (unit: Hz) of the acquisition frequency and a decomposition precision (unit: bit) which represents the amount of data per piece of data are set. For a potential conversion section 2, meanwhile, switching of processing operation between on and off, a set value (unit: Hz) of the acquisition frequency, and a decomposition precision (unit: bit) which represents the amount of data per piece of data are set. For a potential conversion section 3, similarly, switching of processing operation between on and off, a set value (unit: Hz) of the acquisition frequency, and a decomposition precision (unit: bit) which represents the amount of data per piece of data are set. A person in charge of measurement, for example, may set in advance conversion conditions that match an assumed purpose of use for each of the potential conversion sections 1 to 3.

Next, the function of the biopotential measurement device 10 according to the first exemplary embodiment will be described with reference to FIG. 6. In the present exemplary embodiment, a first conversion condition for obtaining a short-term biopotential of the person to be measured Lb and a second conversion condition for obtaining a medium-to-long-term biopotential of the person to be measured Lb are set in advance. The biopotential according to the present exemplary embodiment may be a brain wave potential, a pulse wave potential, a myoelectric potential, etc. The "short-term" represents a period of several minutes to several tens of minutes, for example. The "medium-to-long-term" represents a period of about one day, for example.

Figure 6:
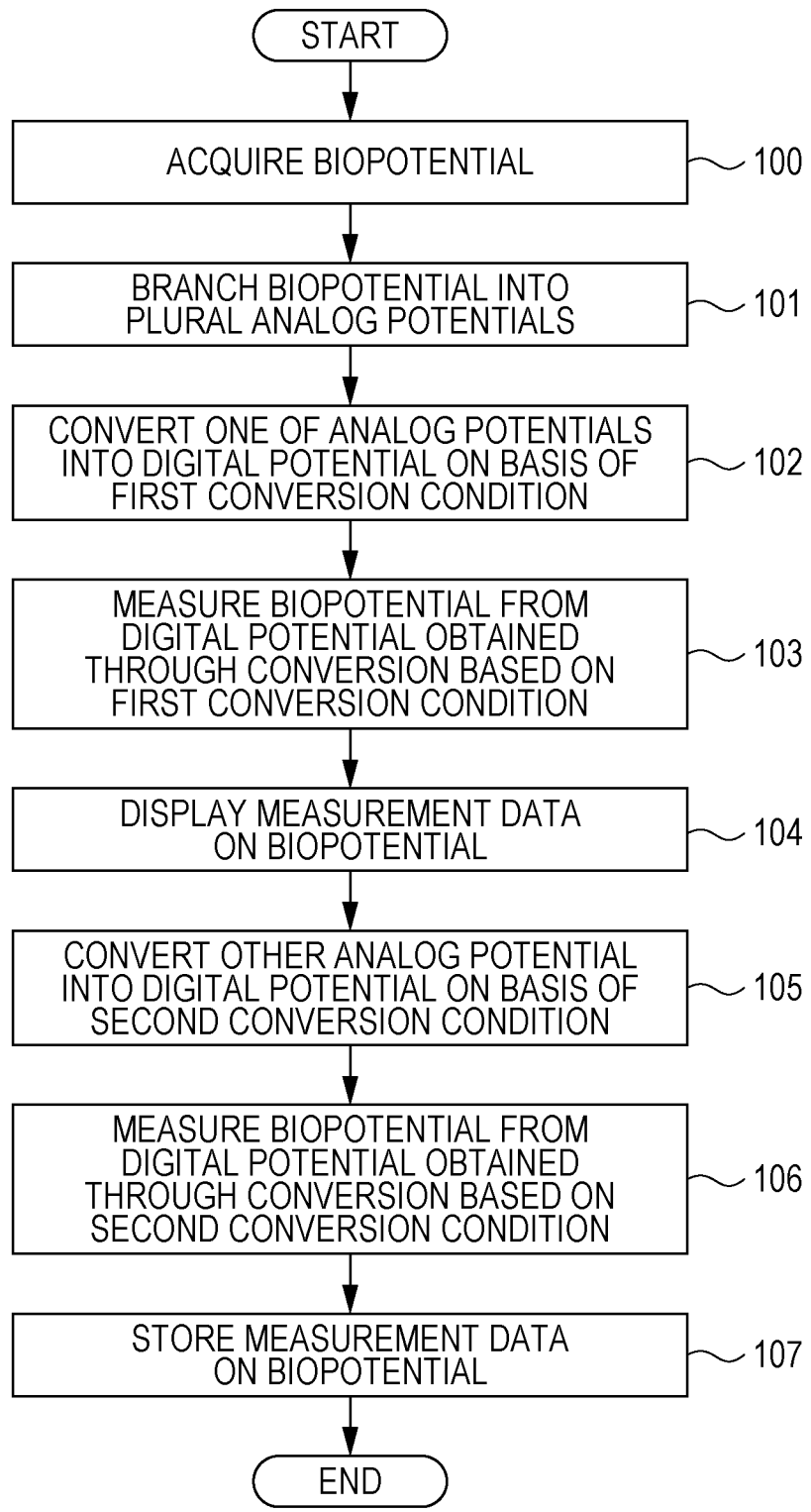
FIG. 6 is a flowchart illustrating an example of the flow of a biopotential measurement process according to the first exemplary embodiment.

FIG. 6 is a flowchart illustrating an example of the flow of a biopotential measurement process according to the first exemplary embodiment.

First, when the biopotential measurement device 10 is instructed to start the biopotential measurement process, the following steps are executed by starting the biopotential measurement program 16A which controls operation of the various sections.

In step 100 of FIG. 6, the analog potential branching section 12 acquires a biopotential (a brain wave potential in the present exemplary embodiment) from the person to be measured Lb via the potential acquisition section 11.

In step 101, the analog potential branching section 12 branches the biopotential acquired in step 100 into a plurality of analog potentials, supplies one of the branched analog potentials to the first AD conversion section 14A, and supplies the other of the branched analog potentials to the second AD conversion section 15A.

In step 102, the first AD conversion section 14A converts one of the analog potentials supplied from the analog potential branching section 12 into a digital potential on the basis of the first conversion condition. Specifically, the first conversion condition may be a condition for obtaining a brain wave potential with a relatively high precision, that is, with a relatively large amount of data, for a short term. For the first conversion condition, by way of example, the acquisition frequency is set to 1000 [Hz], the potential acquisition range is set to 0 [μV] or more and 300 [μV] or less, and the number of bits per piece of data is set to 10 bits. The number of bits per piece of data is determined in accordance with the ratio between the potential acquisition range and the potential acquisition resolution.

In step 103, the first potential measurement section 14B measures a biopotential from the digital potential obtained through the conversion performed on the basis of the first conversion condition in step 102, and supplies measurement data on the biopotential to the CPU 17.

In step 104, the CPU 17 performs control so as to transmit the measurement data on the biopotential supplied from the first potential measurement section 14B to the terminal device 30 via the communication section 19 and display the measurement data on the biopotential on the terminal device 30. Specifically, in the case where it is desired to grasp a short-term concentration level during program preparation work etc., for example, measurement data at a relatively high acquisition frequency are displayed in real time on the terminal device 30 as frequency analysis data for every second.

In step 105, the second AD conversion section 15A converts the other of the analog potentials supplied from the analog potential branching section 12 into a digital potential on the basis of the second conversion condition. Specifically, the second conversion condition may be a condition for obtaining a brain wave potential with a relatively low precision, that is, with a relatively small amount of data, for a medium-to-long term. For the second conversion condition, by way of example, the acquisition frequency is set to 500 [Hz], the potential acquisition range is set to 1 [μV] or more and 300 [μV] or less, and the number of bits per piece of data is set to 10 bits.

In step 106, the second potential measurement section 15B measures a biopotential from the digital potential obtained through the conversion performed on the basis of the second conversion condition in step 105, and supplies measurement data on the biopotential to the CPU 17.

In step S107, the CPU 17 performs control so as to store the measurement data on the biopotential supplied from the second potential measurement section 15B in the memory 16, and ends the biopotential measurement process. Specifically, in the case where it is desired to grasp a medium-to-long-term achievement index, a sustaining time, etc. during program preparation work etc., for example, measurement data (RAW data) at a relatively low acquisition frequency are stored and analyzed. The order of the processes in steps 102 to 104 and the processes in steps 105 to 107 may be reversed. Alternatively, the processes in steps 102 to 104 and the processes in steps 105 to 107 may be executed concurrently.

As described above, the frequency analysis data for every second obtained from the measurement data for the first conversion condition with a relatively high acquisition frequency are displayed in real time on the terminal device 30, and the measurement data for the second conversion condition at a relatively low acquisition frequency are stored in the memory 16. That is, measurement data for a medium-to-long term may also be stored by storing measurement data with a relatively small amount of data in the memory 16.

In this manner, in the present exemplary embodiment, a plurality of systems of potential conversion sections with different conversion conditions are provided in accordance with the purpose of use.

Second Exemplary Embodiment

In the first exemplary embodiment described above, one type of biopotential is selectively measured among a plurality of types of biopotentials. In the present exemplary embodiment, a plurality of types of biopotentials are measured concurrently.

FIG. 7 is a block diagram illustrating an example of the electrical configuration of a biopotential measurement device 10A according to a second exemplary embodiment. Constituent elements that have substantially the same function as those of the biopotential measurement device 10 described in relation to the first exemplary embodiment are given the same reference numeral to omit repeated description.

As illustrated in FIG. 7, the biopotential measurement device 10A according to the present exemplary embodiment includes a potential acquisition section 20, an analog potential branching section 21, an analog potential amplification section 13, a first potential conversion section 14, a second potential conversion section 15, a memory 16, a CPU 17, a frequency analysis section 18, and a communication section 19.

The potential acquisition section 20 acquires a plurality of types of biopotentials from the person to be measured Lb. By way of example, the plurality of types of biopotentials may include some of a brain wave potential, a pulse wave potential, and a myoelectric potential.

The analog potential branching section 21 branches each of the plurality of types of biopotentials acquired by the potential acquisition section 20 into analog potentials. The analog potential branching section 21 supplies an analog potential which represents one of the plurality of types of biopotentials to the first AD conversion section 14A, and supplies an analog potential which represents the other of the plurality of types of biopotentials to the second AD conversion section 15A.

In this case, the first AD conversion section 14A converts the analog potential which represents one of the plurality of types of biopotentials into a digital potential on the basis of the first conversion condition. The second AD conversion section 15A converts the analog potential which represents the other of the plurality of types of biopotentials into a digital potential on the basis of the second conversion condition.

One of the plurality of types of biopotentials may be a brain wave potential, for example. In this case, for the first conversion condition, by way of example, the acquisition frequency is set to 500 [Hz], the potential acquisition range is set to 0 [μV] or more and 300 [μV] or less, and the number of bits per piece of data is set to 10 bits. Meanwhile, the other of the plurality of types of biopotentials may be a myoelectric potential, for example. In this case, for the second conversion condition, by way of example, the acquisition frequency is set to 500 [Hz], the potential acquisition range is set to 0 [μV] or more and 80000 [μV] or less, and the number of bits per piece of data is set to 8 bits. The plurality of types of biopotentials may include three potentials, namely a brain wave potential, a pulse wave potential, and a myoelectric potential. In this case, a potential conversion section may be provided for each of the brain wave potential, the pulse wave potential, and the myoelectric potential (i.e. a total of three potential conversion sections).

As described above, measurement data on two or more biopotentials, among a brain wave potential, a pulse wave potential, and a myoelectric potential, of the person to be measured Lb are stored in the memory 16 with an appropriate acquisition frequency, potential acquisition range, and potential acquisition resolution. For example, in order to grasp the effect of fitness for one hour, measurement data on a brain wave potential are stored in the memory 16 with an acquisition frequency, a potential acquisition range, and a potential acquisition resolution that are appropriate for the brain wave potential. Further, measurement data on a myoelectric potential generated through motion are stored in the memory 16 with an acquisition frequency, a potential acquisition range, and a potential acquisition resolution that are appropriate for the myoelectric potential.

In this manner, in the present exemplary embodiment, in the case where a plurality of types of biopotentials are to be measured concurrently, measurement data are stored with an appropriate acquisition frequency, potential acquisition range, and potential acquisition resolution that are appropriate for each of the plurality of types of biopotentials.

Third Exemplary Embodiment

In the present exemplary embodiment, a case where an external device is operated in accordance with a measured brain wave potential using a brain computer interface function will be described. The term "brain computer interface function" as used herein refers to a function of operating an external device in accordance with a brain wave signal of a person to be measured.

FIG. 8 is a block diagram illustrating an example of the electrical configuration of a biopotential measurement device 10B according to a third exemplary embodiment. Constituent elements that have substantially the same function as those of the biopotential measurement device 10 described in relation to the first exemplary embodiment are given the same reference numeral to omit repeated description.

As illustrated in FIG. 8, the biopotential measurement device 10B according to the present exemplary embodiment includes a potential acquisition section 11, an analog potential branching section 12, an analog potential amplification section 13, a first potential conversion section 14, a second potential conversion section 15, a memory 16, a CPU 17, a frequency analysis section 18, and a brain computer interface (BCI) 22.

The BCI 22 is an interface that connects between the brain of the person to be measured Lb and the external device in order to implement the brain computer interface function discussed above. That is, the BCI 22 is an interface for operating an external device 40 in accordance with a brain wave signal obtained from the brain of the person to be measured Lb. The external device 40 is not specifically limited as long as it is a device to be operated by the person to be measured Lb. Examples of the external device 40 include an input device such as a keyboard.

In this case, the first potential measurement section 14B measures a brain wave potential from the digital potential obtained through the conversion performed by the first AD conversion section 14A. For the first conversion condition, by way of example, the acquisition frequency is set to 2000 [Hz], the potential acquisition range is set to 0 [μV] or more and 300 [μV] or less, and the number of bits per piece of data is set to 10 bits. The second potential measurement section 15B measures a brain wave potential from the digital potential obtained through the conversion performed by the second AD conversion section 15A. For the second conversion condition, by way of example, the acquisition frequency is set to 100 [Hz], the potential acquisition range is set to 0 [μV] or more and 300 [μV] or less, and the number of bits per piece of data is set to 10 bits.

The CPU 17 performs control so as to transmit each of the brain wave potential measured by the first potential measurement section 14B and the brain wave potential measured by the second potential measurement section 15B to the external device 40 via the BCI 22.

That is, in order to execute the brain computer interface function, the biopotential measurement device 10B according to the present exemplary embodiment measures brain wave potentials in a wide frequency range, and operates the external device 40 using the measured brain wave potentials. For example, in the case where the external device 40 such as a keyboard connected via the BCI 22 is operated, frequency analysis data for every second obtained from the measurement data for the first conversion condition with a relatively high acquisition frequency and frequency analysis data for every second obtained from the measurement data for the second conversion condition with a relatively low acquisition frequency are transmitted to the external device 40.

In this manner, in the present exemplary embodiment, brain wave potentials are measured and obtained in a wide frequency range in order to execute the brain computer interface function.

Fourth Exemplary Embodiment

In the present exemplary embodiment, a case where one of a plurality of potential conversion sections measures a biopotential with a high precision while the other potential conversion section is stopped will be described.

FIG. 9 is a block diagram illustrating an example of the electrical configuration of a biopotential measurement device 10C according to a fourth exemplary embodiment. Constituent elements that have substantially the same function as those of the biopotential measurement device 10 described in relation to the first exemplary embodiment are given the same reference numeral to omit repeated description.

As illustrated in FIG. 9, the biopotential measurement device 10C according to the present exemplary embodiment includes a potential acquisition section 11, an analog potential branching section 12, an analog potential amplification section 13, a first potential conversion section 14, a second potential conversion section 15, a memory 16, a CPU 17, a frequency analysis section 18, and a communication section 19.

In this case, the first potential measurement section 14B measures a brain wave potential from the digital potential obtained through the conversion performed by the first AD conversion section 14A. For the first conversion condition, by way of example, the acquisition frequency is set to 2000 [Hz], the potential acquisition range is set to 0 [μV] or more and 500 [μV] or less, and the number of bits per piece of data is set to 10 bits. The second potential measurement section 15B measures a brain wave potential from the digital potential obtained through the conversion performed by the second AD conversion section 15A.

The CPU 17 performs control so as to stop the first potential conversion section 14 including the first AD conversion section 14A and the first potential measurement section 14B or the second potential conversion section 15 including the second AD conversion section 15A and the second potential measurement section 15B. In the present exemplary embodiment, the second potential conversion section 15 is stopped since the first conversion condition is set for the first potential conversion section 14. The first potential conversion section 14 may be stopped in the case where the first conversion condition is set for the second potential conversion section 15.

That is, the biopotential measurement device 10C according to the present exemplary embodiment stores measurement data (RAW data) for the first conversion condition with a relatively high acquisition frequency in the memory 16, and stops the potential conversion section which is not used. The measurement data for the first conversion condition are used in the case where variations in feeling etc. are closely investigated in marketing etc., for example.

In this manner, in the present exemplary embodiment, one of a plurality of potential conversion sections measures a biopotential with a high precision while the other potential conversion section is stopped.

In the embodiments above, the term "processor" refers to hardware in a broad sense. Examples of the processor include general processors (e.g., CPU: Central Processing Unit) and dedicated processors (e.g., GPU: Graphics Processing Unit, ASIC: Application Specific Integrated Circuit, FPGA: Field Programmable Gate Array, and programmable logic device).

In the embodiments above, the term "processor" is broad enough to encompass one processor or plural processors in collaboration which are located physically apart from each other but may work cooperatively. The order of operations of the processor is not limited to one described in the embodiments above, and may be changed.

The biopotential measurement devices according to the exemplary embodiments have been described above. The exemplary embodiments may be implemented in the form of a program that causes a computer to execute control of the various sections of the biopotential measurement devices. The exemplary embodiments may be implemented in the form of a computer-readable storage medium that stores such a program.

Besides, the configuration of the biopotential measurement device described in relation to the above exemplary embodiments is exemplary, and may be changed in accordance with the situation without departing from the scope and spirit of the present disclosure.

The flow of the process of the program described in relation to the above exemplary embodiments is also exemplary, and an unnecessary step may be removed, a new step may be added, or the process order may be changed without departing from the scope and spirit of the present disclosure.

In the exemplary embodiments described above, the process according to the exemplary embodiments is implemented by a software configuration using a computer by executing a program. However, the present disclosure is not limited thereto. For example, the process according to the exemplary embodiments may be implemented by a hardware configuration or a combination of a hardware configuration and a software configuration.

What is claimed is:

1. A biopotential measurement device comprising:
a branching section that branches a biopotential, which is acquired in analog potentials, into a plurality of portions;
a first conversion section that converts one portion of the analog potentials branched by the branching section into a digital potential on a basis of a designated first conversion condition; and
a second conversion section that converts a different portion of the analog potentials branched by the branching section into a digital potential on a basis of a second conversion condition, an amount of data obtained after a conversion with the second conversion condition being smaller than an amount of data obtained after a conversion with the first conversion condition.

2. The biopotential measurement device according to claim 1,
wherein the first conversion condition and the second conversion condition are a frequency acquired from the one portion of the analog potentials and a frequency acquired from the different portion of the analog potentials, respectively, and
the frequency for the second conversion condition is lower than the frequency for the first conversion condition.

3. The biopotential measurement device according to claim 1,
wherein the first conversion condition and the second conversion condition are a potential range and a potential resolution acquired from the one portion of the analog potentials and a potential range and a potential resolution acquired from the different portion of the analog potentials, respectively, and
a ratio between the potential range and the potential resolution for the second conversion condition is lower than a ratio between the potential range and the potential resolution for the first conversion condition.

4. The biopotential measurement device according to claim 2,
wherein the first conversion condition and the second conversion condition are a potential range and a potential resolution acquired from the one portion of the analog potentials and a potential range and a potential resolution acquired from the different portion of the analog potentials, respectively, and
a ratio between the potential range and the potential resolution for the second conversion condition is lower than a ratio between the potential range and the potential resolution for the first conversion condition.

5. The biopotential measurement device according to claim 3, further comprising
a first measurement section that measures the biopotential from the digital potential obtained through a conversion performed by the first conversion section,
a second measurement section that measures the biopotential from the digital potential obtained through a conversion performed by the second conversion section, and
a controller that performs control so as to display the biopotential measured by the first measurement section, and that performs control so as to store the biopotential measured by the second measurement section.

6. The biopotential measurement device according to claim 4, further comprising
a first measurement section that measures the biopotential from the digital potential obtained through a conversion performed by the first conversion section,
a second measurement section that measures the biopotential from the digital potential obtained through a conversion performed by the second conversion section, and
a controller that performs control so as to display the biopotential measured by the first measurement section, and that performs control so as to store the biopotential measured by the second measurement section.

7. The biopotential measurement device according to claim 3,
wherein the biopotential includes a plurality of types of biopotentials,
an analog potential that represents one of the plurality of types of biopotentials is converted into a digital potential in accordance with the first conversion condition, and
an analog potential that represents the other of the plurality of types of biopotentials is converted into a digital potential in accordance with the second conversion condition.

8. The biopotential measurement device according to claim 4,
wherein the biopotential includes a plurality of types of biopotentials,
an analog potential that represents one of the plurality of types of biopotentials is converted into a digital potential in accordance with the first conversion condition, and
an analog potential that represents the other of the plurality of types of biopotentials is converted into a digital potential in accordance with the second conversion condition.

9. The biopotential measurement device according to claim 3,
wherein the biopotential measurement device is connected to an external device via a brain computer interface function,
the biopotential is a brain wave potential, and
the biopotential measurement device further includes
a first measurement section that measures the brain wave potential from the digital potential obtained through a conversion performed by the first conversion section,
a second measurement section that measures the brain wave potential from the digital potential obtained through a conversion performed by the second conversion section, and
a controller that performs control so as to transmit each of the brain wave potential measured by the first measurement section and the brain wave potential measured by the second measurement section to the external device.

10. The biopotential measurement device according to claim 4,
wherein the biopotential measurement device is connected to an external device via a brain computer interface function,
the biopotential is a brain wave potential, and
the biopotential measurement device further includes
a first measurement section that measures the brain wave potential from the digital potential obtained through a conversion performed by the first conversion section, a second measurement section that measures the brain wave potential from the digital potential obtained through a conversion performed by the second conversion section, and a controller that performs control so as to transmit each of the brain wave potential measured by the first measurement section and the brain wave potential measured by the second measurement section to the external device.

11. The biopotential measurement device according to claim 3, further comprising a first measurement section that measures the biopotential from the digital potential obtained through a conversion performed by the first conversion section, a second measurement section that measures the biopotential from the digital potential obtained through a conversion performed by the second conversion section, and a controller that performs control so as to stop either the first conversion section and the first measurement section or the second conversion section and the second measurement section.

12. The biopotential measurement device according to claim 4, further comprising a first measurement section that measures the biopotential from the digital potential obtained through a conversion performed by the first conversion section, a second measurement section that measures the biopotential from the digital potential obtained through a conversion performed by the second conversion section, and a controller that performs control so as to stop either the first conversion section and the first measurement section or the second conversion section and the second measurement section.

13. The biopotential measurement device according to claim 1, wherein the first conversion condition and the second conversion condition are each set in advance in accordance with a purpose of use of the biopotential.

14. The biopotential measurement device according to claim 2, wherein the first conversion condition and the second conversion condition are each set in advance in accordance with a purpose of use of the biopotential.

15. The biopotential measurement device according to claim 3, wherein the first conversion condition and the second conversion condition are each set in advance in accordance with a purpose of use of the biopotential.

16. The biopotential measurement device according to claim 4, wherein the first conversion condition and the second conversion condition are each set in advance in accordance with a purpose of use of the biopotential.

17. The biopotential measurement device according to claim 13, further comprising a controller that performs control so as to display a reception screen for receiving setting of each of the first conversion condition and the second conversion condition.

18. The biopotential measurement device according to claim 14, further comprising a controller that performs control so as to display a reception screen for receiving setting of each of the first conversion condition and the second conversion condition.

19. The biopotential measurement device according to claim 15, further comprising a controller that performs control so as to display a reception screen for receiving setting of each of the first conversion condition and the second conversion condition.

20. A non-transitory computer readable medium storing a biopotential measurement program causing a computer to execute a process comprising:

controlling a branching section that branches a biopotential, which is acquired in analog potentials, into a plurality of portions;

controlling a first conversion section that converts one portion of the analog potentials branched by the branching section into a digital potential on a basis of a designated first conversion condition; and controlling a second conversion section that converts the other portion of the analog potentials branched by the branching section into a digital potential on a basis of a second conversion condition, an amount of data obtained after a conversion with the second conversion condition being smaller than an amount of data obtained after a conversion with the first conversion condition.

* * * * *